United States Patent [19]

Buechler et al.

[11] Patent Number: 5,470,997
[45] Date of Patent: Nov. 28, 1995

[54] AMPHETAMINE DERIVATIVES AND PROTEIN AND POLYPEPTIDE AMPHETAMINE DERIVATIVE CONJUGATES AND LABELS

[75] Inventors: Kenneth F. Buechler, San Diego; Joseph B. Noar, Solana Beach; Si S. Moi, Escondido, all of Calif.

[73] Assignee: Biosite Diagnostics Incorporated, San Diego, Calif.

[21] Appl. No.: 864,108

[22] Filed: Apr. 6, 1992

[51] Int. Cl.$^6$ .................... C07C 327/22; C07C 323/41; C07C 323/52
[52] U.S. Cl. ............ 558/254; 560/24; 560/145; 564/192; 564/381; 530/404; 530/408; 436/544
[58] Field of Search .................. 530/404, 408; 435/188, 964; 436/501, 544; 564/440, 192, 381; 558/254; 560/24, 145

[56] References Cited

U.S. PATENT DOCUMENTS

| | | | |
|---|---|---|---|
| 3,878,187 | 4/1975 | Schneider et al. | 436/547 |
| 4,016,146 | 4/1977 | Soares | 530/363 |
| 4,067,774 | 1/1978 | Rubenstein et al. | 435/188 |
| 4,069,105 | 1/1978 | Singh | 436/816 |
| 4,232,119 | 11/1980 | Carlsson et al. | 435/7.9 |
| 4,328,311 | 5/1982 | Rowley et al. | 530/405 |
| 4,329,281 | 5/1982 | Christenson et al. | 530/363 |
| 4,695,624 | 9/1987 | Marburg et al. | 530/404 |
| 4,868,132 | 9/1989 | Brynes et al. | 436/546 |
| 4,952,336 | 8/1990 | Brynes et al. | 252/301.16 |
| 5,135,863 | 8/1992 | Hu et al. | 435/7.9 |

FOREIGN PATENT DOCUMENTS

| | | |
|---|---|---|
| 0284413 | 9/1988 | European Pat. Off. . |
| 0375422 | 6/1990 | European Pat. Off. . |
| 0371253 | 6/1990 | European Pat. Off. . |
| 9218866 | 10/1992 | WIPO . |

OTHER PUBLICATIONS

Blair et al (1983) J. Immunol. Methods 59: 129–143.
Gallacher et al (1989) Therapeutic Drug Monitoring 11: 607–611.
Rowley et al (1975) J. Biol. Chem. 250(10): 3759–3766.
Terzawa et al. (1991) J. Immunoassay 12(2): 277–292.
Abstract No. 204 Molina, et al., published in Clin. Chem. 31:941–42 (1985).
Faraj, Bahjat, A. et al., Specificity of an Antibody Directed against d–Methamphetamine. Studies with Rigid and Non-rigid Analogs, J. Med. Chem. 19:21–25 (1976).

Primary Examiner—Kay K. A. Kim
Attorney, Agent, or Firm—Lyon & Lyon

[57] ABSTRACT

The present invention is directed to novel amphetamine derivatives which are synthesized for the covalent attachment to antigens (proteins or polypeptides) for the preparation of antibodies or receptors to amphetamine and amphetamine metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

2 Claims, 1 Drawing Sheet

EXAMPLE 4

EXAMPLE 10

EXAMPLE 5

EXAMPLE 11

EXAMPLE 14

EXAMPLE 7

EXAMPLE 15

AMPHETAMINE DERIVATIVES AND PROTEIN AND POLYPEPTIDE AMPHETAMINE DERIVATIVE CONJUGATES AND LABELS

FIELD OF THE INVENTION

This invention is in the field of ligand receptor assays, including immunoassays, for the detection of selected metabolites of amphetamine and methamphetamine (amphetamine) in a fluid sample. More particularly, this invention relates to methods for the synthesis of novel amphetamine derivatives and protein and polypeptide amphetamine derivative conjugates and labels for use in the preparation of antibodies to amphetamine and amphetamine metabolites and for use in the immunoassay process.

BACKGROUND OF THE INVENTION

Amphetamine and methamphetamine stimulate the central nervous system and have been used medicinally to treat hypotension, narcolepsy and obesity. Because of their stimulating effects the drugs and derivatives have been abused. The illicit use of amphetamine and amphetamine analogues, such as p-methoxyamphetamine, methylenedioxyamphetamine, 2,5-dimethoxy-4-methylamphetamine, 2,4,5-trimethoxyamphetamine and 3,4-methylenedioxymethamphetamine has resulted in a medical need for antibodies and diagnostics to rapidly detect the amphetamine metabolites in order to monitor and treat amphetamine addiction.

The preparation of antibodies to amphetamine requires the synthesis of an amphetamine derivative in order to covalently attach the derivative to an antigenic polypeptide or protein. In addition, the amphetamine derivative is covalently attached to various polypeptides, proteins or labels for use in screening antibodies and in the immunoassay process. The amphetamine derivative should mimic the structure of the amphetamine metabolite sought to be measured. Therefore, the selection and synthesis of the types of amphetamine derivatives for covalent attachment to proteins, polypeptides or labels is critical. In addition, the amphetamine derivatives need to be stable to hydrolysis in an aqueous solution.

SUMMARY OF THE INVENTION

The present invention is directed to novel amphetamine derivatives which are synthesized for the covalent attachment to antigens (proteins or polypeptides) for the preparation of antibodies to amphetamine and amphetamine metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are morphine, barbiturates, tetrahydrocannabinol, phencyclidine, amphetamines, methamphetamines, opiates, benzodiazepines, cocaine, estrone-3-glucuronide, pregnanediol-glucuronide, cotinine, lysergic acid diethylamide, propoxyphene, methadone, anabolic steroids, tricyclic antidepressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Amphetamine" shall mean any of the sympathomimetic phenethylamine derivatives which have central nervous system stimulant activity, such as but not limited to, amphetamine, methamphetamine, p-methoxyamphetamine, methylenedioxyamphetamine, 2,5-dimethoxy-4-methylamphetamine, 2,4,5-trimethoxyamphetamine and 3,4-methylenedioxymethamphetamine.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the "chemical arm" between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1- or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the $-C_6H_4-Ar$ substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl-CO— or HCO—.

The terms "acylamino" refers to RCONCR)— and (RCO₂N— respectively, wherein each R is independently hydrogen or hydrocarbyl.

The term "hydrocarbyloxycarbonyloxy" shall refer to the group ROC(O)O— wherein R is hydrocarbyl.

The term "lower carboalkoxymethyl" or "lower hydrocarbyloxycarbonylmethyl" refers to hydrocarbyl-OC(O)CH₂— with the hydrocarbyl group containing ten or less carbon atoms.

The term "carbonyl" refers to —C(O)—.

The term "carboxamide" or "carboxamido" refers to —CONR₂ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl-O—CONR— wherein R is H or hydrocarbyl and wherein each hydrocarbyl is independently selected.

The term "di(hydrocarbyloxycarbonyl)amino" refers to (hydrocarbyl-O—CO)₂N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methine" refers to

The term "methylene" refers to —CH₂—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thioester" refers to

"Thioether" refers to c—S—C.

"Ester" refers to

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefore, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DETAILED DESCRIPTION OF THE PREFERRED EMBODIMENTS

Figure 1:
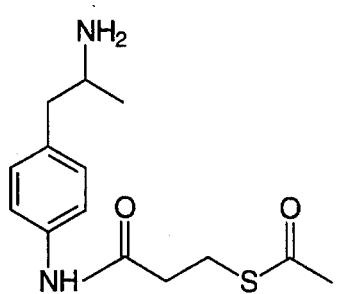
FIG. 1 depicts the structures of the compounds of Examples 4, 5, 7, 10, 11, 14 and 15.
Figure 1:
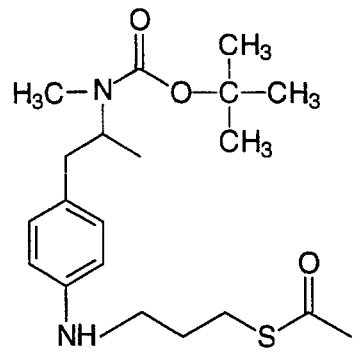
Figure 1:
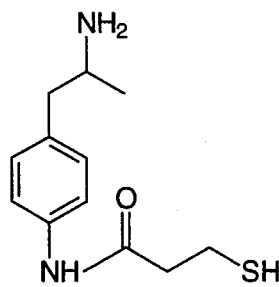
Figure 1:
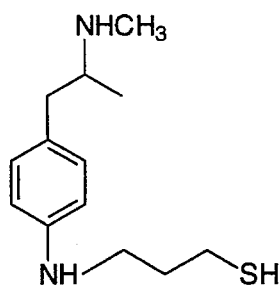
Figure 1:
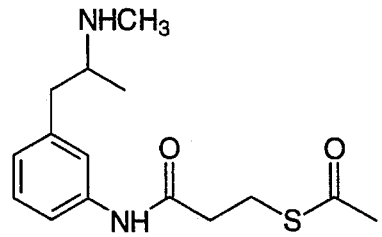
Figure 1:
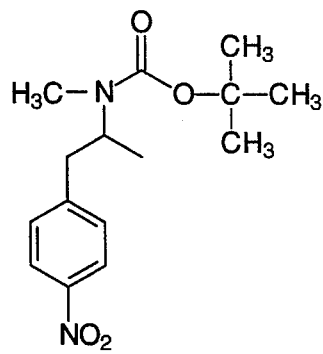
Figure 1:
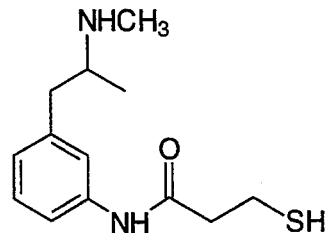

Novel compounds are described which are used in the generation of antibodies and in the immunoassay process generally. The compounds are derivatives of amphetamine and the amphetamine metabolites. The derivatization of amphetamine or amphetamine analogues for covalent attachment to proteins, polypeptides and labels occurs on the phenyl ring so that the character of the aliphatic amine is extended from the surface of the molecular structure in order to be presented to the antibody or receptor in a manner which allows for the desired binding interaction. The synthesis of the linking group between the protein, polypeptide or label and the amphetamine derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the following formula:

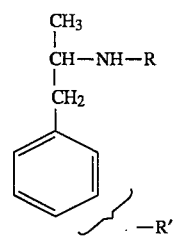

where R is —H, —CH$_3$
where R' is an ortho, meta or para linking group comprising one of the following;

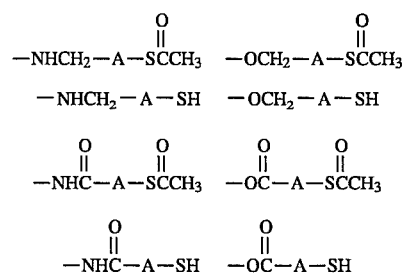

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label to a compound of the formula is of the following:

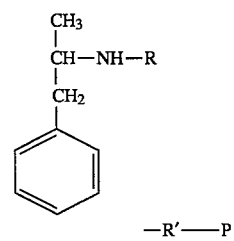

where P is an antigenic protein or polypeptide or a protein, polypeptide or label;
where x is at least one and not greater than 100;
where R is —H, —CH$_3$
where R' is a linking group of the following:

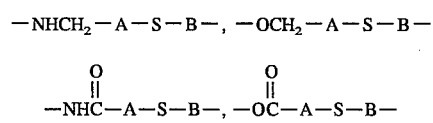

where A is a linking group of from 1 to 20 carbons and 0 to 10 heteroatoms (NH, O, S) either branched or straight chain;
where B is a linking group ultimately attached to a protein, polypeptide or label selected from the group comprising:

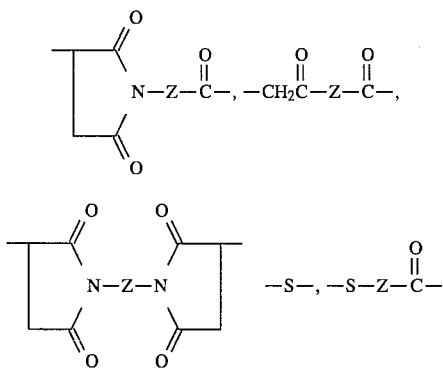

where Z is a linking group of from 1 to 20 carbons and 0 to 10 heteroatoms (NH, O, S) and may be branched or straight chain. The preferred (best mode) compounds of this invention have the following formula:

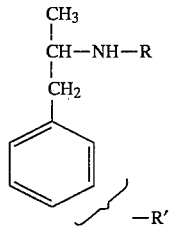

where R is —H, —CH$_3$ where R' is a linking group comprising one of the following;

$$-NHCH_2CH_2CH_2SCCH_3$$ (with C=O)

—NHCH$_2$CH$_2$CH$_2$SH

—NHCCH$_2$CH$_2$SCCH$_3$ (with two C=O)

—NHCCH$_2$CH$_2$SH (with C=O)

In addition, the preferred (best mode) immunogenic protein or polypeptide molecule or the protein or polypeptide molecule or label derivatized via an amide or ester bond to the molecule or label to a compound of the formula is of the following:

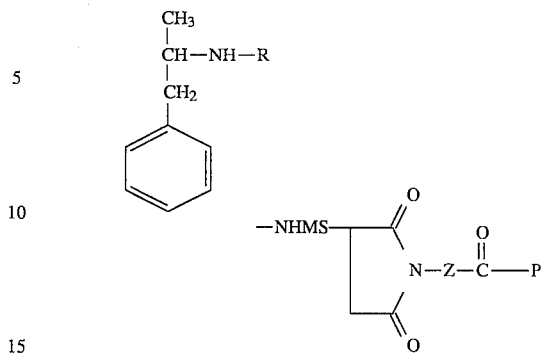

where P is an antigenic protein or polypeptide or a protein, polypeptide or label;

where x is at least one and not greater than 100;

where R is —H, —CH$_3$ where M is

—CH$_2$CH$_2$CH$_2$— where Z is a linking group of from 1 to 20 carbons and 0 to 10 heteroatoms (NH, O, S) and may be branched or straight chain.

Of particular interest are amphetamine derivatives which have been synthesized using the d-stereoisomer. The d-isomers of amphetamine have more central stimulant activity than the l-isomers. The l-isomers are used as decongestants and therefore antibodies used to monitor illicit drug abuse must distinguish between the d- and l-isomers. The compounds of the present invention are synthesized as the d-isomers to distinguish the legal use of the l-isomer from the abuse of the d-isomer. In addition, if highly specific antibodies to the d-isomers of amphetamine are required then the presentation of the aliphatic amine portion of the amphetamine to the antibody is important. The amphetamine derivatives are substituted off the phenyl ring at the ortho, meta and para positions, preferably at the meta and para positions, to provide the proper presentation. The elaboration of the linking group off the aromatic amine or off an aromatic hydroxyl of, for example, a t-boc protected amphetamine, can be performed using various chain length alkyl halide carboxylic acids, for example, 3-iodopropionic acid to form an N-alkylated or O-alkylated carboxylic acid amphetamine derivative, respectively, which can then be further reacted with an amino alkyl thiol ester, such as homocysteine thiolactone, to synthesize the thiol ester derivative of the amphetamine (after deprotection of the aliphatic amine in acid). In addition, the linking group can be elaborated from the aromatic amine or hydroxyl using various chain lengths of carboxylic acid alkyl thiol esters, for example, 3-acetylthiol propionic acid. The thio esters are hydrolyzed in dilute base, for example, 0.01 M potassium hydroxide, to generate the thiol group which is reacted with the thiol reactive group, such as a maleimide, an alkyl halide or a thiol. Those skilled in the art can recognize the versatility of synthetic strategies described herein.

The compounds are synthesized as thiols or thiol esters so that their covalent attachment to proteins, polypeptides or labels can easily be performed under mild conditions, for example, pH 7 in a protein solution. The protein, polypeptide or label is reacted with a reagent which incorporates a maleimide or alkylhalide into the molecule. These reagents and methods for their use are available from Pierce, Rockford, Ill., for example, for incorporation of maleimide groups onto proteins, polypeptides or labels one can use succinimidyl 4-(N-maleimidomethyl)cyclohexane- 1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl)aminobenzoate (SIAB) also from Pierce. The thiol reactive group, such as maleimide, an alkyl halide or a thiol can be incorporated into the protein, polypeptide or label prior to reaction with the drug thiol but the drug thiol can also be reacted with the thiol reactive compound prior to reaction with the protein, polypeptide or label. Also, bismaleimide compounds of varying length can be reacted with thiol containing proteins, polypeptides or labels for covalent coupling of the amphetamine thiol derivatives. Conversely, the bis-maleimide compound can be reacted with the thiol derivative and subsequently to the thiol containing protein, polypeptide or label. Common bis-maleimides are bis-maleimidohexane from Pierce, N,N'-bis( 3-maleimidopropionyl)-2-hydroxy-1,3-propanediamine from Sigma Chemical Co., St Louis, Mo., and 1,1'-(methylenedi- 4,1-phenylene)-bismaleimide from Aldrich Chem. Co., Milwaukee, Wis. The thiol amphetamine derivatives can also form disulfides with thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 4,067,774, 4,952,336, 5,028,535 and 5,089,391.

EXPERIMENTAL EXAMPLES

Example 1

Synthesis of p-Nitro-d-Amphetamine Hydrochloride d-Amphetamine sulfate (10 g, 2.7×10$^{-4}$ mol) was dissolved in sulfuric acid (5 mL), and the solution was cooled in an ice-water bath. Fuming nitric acid (4.6 mL) was added dropwise to the reaction solution. The reaction mixture was stirred for 1 h. The mixture was poured over ice-water and 10N sodium hydroxide was added to adjust the solution to pH 12. The mixture was extracted with diethyl ether (2×100 mL), the combined organic layers were washed with water (2×100 mL), and dried over anhydrous magnesium sulfate. The drying agent was removed by filtration, and hydrochloric acid (1N) in diethyl ether was added to form the hydrochloride salt. The solvent was removed under vacuum. Acetone (200 mL) was added to the white residue and stirred at room temperature for 2 h. The slurry suspension was then filtered, and the resulting white precipitate was recrystallized from ethanol/acetone to yield 3.5 g (60%) of p-nitro-amphetamine hydrochloride as a white crystalline solid: mp 191°–192° C.

Example 2

Synthesis of p-Amino-d-Amphetamine Dihydrochloride p-Nitro-d-amphetamine hydrochloride (3.5 g, 1.6×10$^{-4}$ mol) was dissolved in methanol (200 mL) followed by the addition of 10% palladium-carbon (1.0 g) and ammonium formate (7.0 g). The reaction mixture was stirred at room temperature for 2 h. The catalyst was removed by filtration and the solvent removed under vacuum. The partially crystalline residue was re-dissolved in water (20 mL) and potassium hydroxide pellets were added to adjust the solution to pH 12. The solution was then extracted with methylene chloride (3×60 mL), the combined organic layers were washed with water (1×50 mL), and dried over anhydrous magnesium sulfate. The drying agent was removed by filtration, and hydrochloric acid (1N) in diethyl ether was added to form the hydrochloride salt. The solvent was removed under vacuum to give 2.0 g (56%) of p-amino-d-amphetamine dihydrochloride as a white crystalline solid: mp 225°–240° C.

Example 3

Synthesis of Acetylthiopropionic Acid

To a stirred solution of 3-mercaptopropionic acid (7 ml, 8×10$^{-2}$ moles) and imidazole (5.4 g, 8×10$^{-2}$ moles) in tetrahydrofuran (THF, 700 ml) was added dropwise over 15 minutes, under argon, a solution of 1-acetyl imidazole (9.6 g, 8.7×10$^{-2}$ moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5–2. The mixture was extracted with diethyl ether (2×50 ml), the ether was washed with water (2×50 ml), and dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44°–45° C.

Example 4

Synthesis of P-Acetylthiopropionamide-d-Amphetamine Phosphate

To a stirring solution of acetylthiopropionic acid (1.46 g, 9.8×10$^{-3}$ mol) in anhydrous dimethylformamide (44 ml) was added 1,1'-carbonyldiimidazole (1.74 g, 10.7×10$^{-3}$ mol). After stirring for 45 minutes at room temperature this solution was added to a stirring solution of p-amino-d-amphetamine dihydrochloride (2.0 g, 9.0×10$^{-3}$ mol) in anhydrous dimethylformamide (44 ml) containing hydrogen chloride (1N) in diethyl ether (22 ml, 2.2×10$^{-2}$ mol). The flask was purged with argon and the solution stirred at room temperature for 1 hour. The solvent was evaporated under vacuum and the residue evaporated twice from ethyl alcohol (50 ml). The residue was treated with methylene chloride (40 ml) and the insoluble imidazole filtered. The filtrate was evaporated under vacuum, the residue dissolved in water (50 ml) and washed twice with methylene chloride (50 ml). The aqueous solution was evaporated under vacuum and the residue was purified on a Vydac reverse phase $C_{18}$ column (5×25 cm) equilibrated in 20 mM potassium phosphate, pH 2.5, at a flow rate of 50 ml/min. The product was eluted with a linear gradient up to 100% methanol in 60 min. Product eluted between 19 and 31 min. The desired fractions were collected and the solvent was removed in vacuo. The residue was dissolved in water and the pH was adjusted to 4.6 with potassium hydroxide (1N). The solvent was removed in vacuo. Methanol was added to the residue and filtered. The solvent of the filtrate was removed in vacuo to yield 1.9 g (31%) of p-acetylthiopropionamide-d-amphetamine phosphate as a white crystalline solid.

Example 5

Synthesis of p-3-Mercaptopropionamide-d-Amphetamine p-Acetylthiopropionamide-d-amphetamine phosphate (0.01 g, $2.4 \times 10^{-5}$ mol) was dissolved in 1.58 ml 0.12M potassium carbonate in 80% methanol/20% water (v/v). The solution sat at room temperature for 5 min and then 0.3 ml 0.5M potassium phosphate, pH 7, was added and the solution was adjusted to pH 7–7.5 with hydrochloric acid (1N). The title compound in solution was used as is to react with thiol reactive groups, such as maleimides, alkyl halides or thiols, which are either free in solution or are coupled to proteins, polypeptides or labels.

Example 6

Synthesis of p-Nitro-d-Methamphetamine Hydrochloride d-Methamphetamine hydrochloride (4.5 g, $2.4 \times 10^{-2}$ mol) was dissolved in sulfuric acid (8.5 ml), and the solution was cooled in an ice-water bath. Fuming nitric acid (1.4 ml) was added dropwise to the solution. The reaction mixture was stirred at 0° C. for 1 h. The solution was poured over ice and 10N sodium hydroxide (35 ml) solution was added to adjust the pH to 12. The aqueous solution was extracted with diethyl ether (3×50 ml). The combined organic layers were washed with deionized water (2×50 ml), and dried over anhydrous magnesium sulfate. The drying agent was removed by filtration and hydrogen chloride (1N) in diethyl ether (25 ml) was added to form the hydrochloride salt. The solvent was removed in vacuo. Acetone (100 ml) was added to the residue and stirred at room temperature for 1 h. The slurry suspension was filtered to give 4.0 g of p-nitromethamphetamine hydrochloride as a white crystalline solid: mp 192°–205° C.

Example 7

Synthesis of t-Butoxycarbonyl-p-Nitro-d-Methamphetamine p-Nitro-d-methamphetamine hydrochloride (4.0 g, $1.7 \times 10^{-2}$ mol) was dissolved in chloroform (70 ml). To the solution, potassium bicarbonate (1.8 g, $1.8 \times 10^{-2}$ mol) dissolved in deionized water (25 ml) was added followed by sodium chloride (7.0 g, $1.2 \times 10^{-1}$ mol). The reaction mixture was stirred until all the solute was in solution. Di-tert-butyl dicarbonate (4.0 g, $1.8 \times 10^{-2}$ mol) dissolved in chloroform (20 ml) was added to the solution, and stirred at room temperature for 1 h. The chloroform layer was collected, and the aqueous layer was extracted with chloroform (50 ml ×1).

The combined organic layers were dried over anhydrous magnesium sulfate. The drying agent was removed by filtration. The solvent was removed in vacuo to give 4.8 g of the title compound as a yellow crystalline solid.

Example 8

Synthesis of t-Butoxycarbonyl-p-Amino-d-Methamphetamine Hydrochloride

Under argon, t-butoxycarbonyl-p-nitro-d-methamphetamine (4.8 g, $1.6 \times 10^{-2}$ mol) was dissolved in methanol (140 ml) followed by the addition of 10% palladium-carbon (1.4 g) and ammonium formate (5.6 g, $8.9 \times 10^{-2}$ mol). The reaction mixture was stirred at room temperature for 2 h. The catalyst was removed by filtration and the solvent removed in vacuo. The residue was partitioned between deionized water (50 ml) and diethyl ether (100 ml). The ether layer was washed with deionized water (50 ml ×1), and dried over anhydrous magnesium sulfate. The drying agent was removed by filtration, and hydrochloric acid (1 N) in diethyl ether (14 ml) was added to form the hydrochloride salt. The solvent was removed in vacuo. Ethyl acetate (50 ml) was added to the residue and stirred at room temperature for 10 min. The suspension was filtered to give 4.0 g of the title compound as a white crystalline solid: mp 160°–165° C.

Example 9

Synthesis of 3-Iodopropylthiolacetate

Sodium iodide (27 g, $1.8 \times 10^{-1}$ mol) was dissolved in acetone (95 ml), and 3-chloropropylthioacetate (3.5 g, $2.3 \times 10^{-2}$ mol) was added to the solution. The reaction mixture was protected from light and refluxed overnight. The solution was cooled to room temperature and the solvent removed in vacuo. Diethyl ether (100 ml) was added to the residue to form a slurry suspension. The insoluble precipitate was filtered and washed with diethyl ether (20 ml×2). The filtrate was evaporated under vacuum to give 4.8 g of 3-iodopropylthiolacetate as a dark brown oil.

Example 10

Synthesis oft-Butoxycarbonyl-p-(3-Acetylthiopropyl)amino-d-Methamphetamine

To a solution of t-butoxycarbonyl-p-amino-d-methamphetamine hydrochloride (4.0 g, $1.3 \times 10^{-2}$ mol) in ethanol (200 proof, 90 ml) was added triethylamine (2.8 g, $2.7 \times 10^{-2}$ mol) followed by 3-iodopropylthiolacetate (3.5 g, $1.4 \times 10^2$ mol). The reaction mixture was refluxed overnight. The solution was cooled to room temperature and the solvent removed in vacuo. Ethyl acetate (100 ml) was added, and the slurry suspension was then filtered to remove the triethylamine salt. The filtrate was evaporated under vacuum to give a dark yellow residue. The residue was triturated with hexane (50 ml×3) and the solvent removed in vacuo to give 3.8 g of the title compound.

Example 11

Synthesis of p-(3-Mercaptopropyl)amino-d-Methamphetamine Phosphate t-Butoxycarbonyl-p-(3-acetylthiopropyl)amino-d-methamphetamine (3.8 g, $1.0 \times 10^{-2}$ mol) was treated with hydrogen chloride (1N) in diethyl ether (100 ml), and stirred at room temperature overnight. The solvent was removed in vacuo. The residue was redissolved in hydrogen chloride (6N, 200 ml), and stirred at 50° C. for 3 h. The solvent was removed in vacuo. The product was dissolved in water and was purified on a Vydac reverse phase $C_{18}$ column (5×25 cm) equilibrated in 50 mM potassium phosphate, pH 2.5, at a flow rate of 50 ml/min. The product was eluted with a linear gradient up to 100% methanol in 60 min. Product eluted between 16 and 19 min. The desired fractions were collected and the solvent was removed in vacuo. The residue was dissolved in water and the pH was adjusted to 4.6 with potassium hydroxide (1N). The solvent was removed in vacuo. Methanol was added to the residue and filtered. The solvent of the filtrate was removed in vacuo to yield 1.5 g of the title compound.

Example 12

Synthesis of mixed isomers of Nitro-d-Methamphetamine Hydrochloride d-Methamphetamine hydrochloride (4.5 g, $2.4 \times 10^{-2}$ mol) was dissolved in sulfuric acid (8.5 ml), and the solution was cooled in an ice-water bath. Fuming nitric acid (1.4 ml) was added dropwise to the solution. The reaction mixture was stirred at 0° C. for 1 h. The solution was poured over ice and 10N sodium hydroxide (35 ml) solution was added to adjust pH to 12. The aqueous solution was extracted with diethyl ether (3×50 ml). The combined organic layers were washed with deionized water (2×50 ml), and dried over anhydrous magnesium sulfate. The drying agent was removed by filtration, and hydrogen chloride (1N) in diethyl ether (25 ml) was added to form the hydrochloride salt. The solvent was removed in vacuo. Acetone (100 ml) was added to the residue and stirred at room temperature for 1 h. The slurry suspension was filtered and the filtrate was evaporated under vacuum to give 2.0 g of mixed isomers of ortho, meta and para nitro-d-methamphetamine hydrochloride as a yellow oil.

Example 13

Synthesis of mixed isomers of Amino-d-Methamphetamine Dihydrochloride

To a solution of mixed isomers of nitro-d-methamphetamine hydrochloride (2.0 g, $8.7 \times 10^{-3}$ mol) in methanol (87 ml) was added 10% palladium-carbon (0.4 g) and ammonium formate (2.1 g, $3.5 \times 10^{-2}$ mol). The reaction mixture was stirred at room temperature for 2 h. The catalyst was removed by filtration and the solvent removed in vacuo. The partially crystalline residue was redissolved in water (20 ml). Potassium hydroxide solution (10N) was added to adjust pH to 12. The solution was extracted with methylene chloride (50 ml×2), the combined organic layers were washed with deionized water (50 ml×1), and dried over anhydrous magnesium sulfate. The drying agent was removed by filtration and hydrogen chloride (1N) in diethyl ether was added to form the dihydrochloride salt. The solvent was removed in vacuo to give 1.0 g of amino-d-methamphetamine dihydrochloride isomers.

Example 14

Synthesis of ortho-, meta-, and para-3-Acetylthiopropionamide-d-Methamphetamine Phosphate To a solution of aminomethamphetamine dihydrochloride isomers (0.3 g, $1.1 \times 10^{-3}$ mol) in anhydrous dimethylformamide (11 ml) containing anhydrous pyridine (0.3 g, $3.3 \times 10^{-3}$ mol) was added acetylthiopropionic acid (0.2 g, $1.1 \times 10^{-3}$ mol). 1-(3-Dimethylaminopropyl)-3-ethylcarbodiimide (0.2 g, $1.2 \times 10^{3}$ mol) was added to the reaction mixture and stirred at room temperature for 2 h. The solvent was removed in vacuo and ethanol (20 ml×2) was added to azeotrope off any residual dimethylformamide to give an orange oil. The crude product was injected onto a Vydac HS Pharmaceutical Analysis reverse phase $C_{18}$ column (1×25 cm) equilibrated in 20 mM potassium phosphate, pH 4.6, at a flow rate of 2 ml/min and the product was eluted with a linear gradient of up to 50% methanol in 50 min. The para isomer eluted between 37.2 and 38 min, the ortho isomer eluted between 40.4 and 43.6 min and the meta isomer eluted between 47.2 and 48.8 min. The desired fractions were collected and the solvents were removed in vacuo. Methanol (10 ml) was added to the residue, the suspension was filtered and the solvent of the filtrate was removed in vacuo to yield 0.03 g of meta-3-acetyl-thiolpropionamide-d-methamphetamine phosphate.

Example 15

Synthesis of meta-3-Mercaptopropionamide-d-Methamphetamine meta-3-Acetylthiopropionamide-d-methamphetamine (4 mg, $9.3 \times 10^{-6}$ mol) was dissolved in 0.46 ml 0.12M potassium carbonate in 80% methanol/20% water (v/v). The solution sat at room temperature for 3 min and then 0.1 ml 0.5M potassium phosphate, pH 7, was added and the solution was adjusted to pH 7–7.5 with hydrochloric acid (1N). The title compound in solution was used as is to react with thiol reactive groups, such as maleimides, alkyl halides or thiols, which are either free in solution or are coupled to proteins, polypeptides or labels.

Other embodiments are within the following claims.

I claim:

1. A compound of the formula:

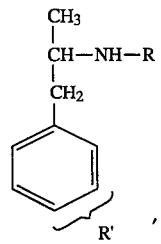

where R is —H, —$CH_3$ where R' is an ortho, meta or para linking group consisting of one of the following;

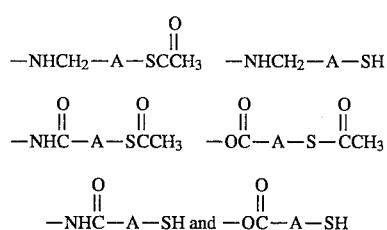
Where A is a linking group of from 1 to 20 carbons and from 0 to 10 heterocarbons (NH, O, S), either branched or straight chain.
2. Compounds of the formula:
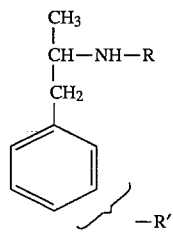
where R is —H, —CH$_3$
where R' is a meta or para linking group consisting of one of the following;
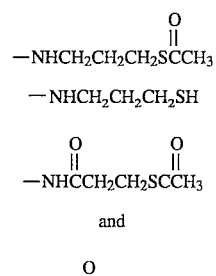
and
$$-NHCCH_2CH_2SH.$$
* * * * *